(12) United States Patent
Mattern

(10) Patent No.: US 6,244,745 B1
(45) Date of Patent: Jun. 12, 2001

(54) DEVICE FOR MOVING AN X-RAY TABLE OR THE LIKE

(75) Inventor: Helmuth Mattern, Grossenseebach (DE)

(73) Assignee: Hans Pausch Rontgengeratebau GmbH & Co., Erlangen (DE)

( * ) Notice: Subject to any disclaimer, the term of this patent is extended or adjusted under 35 U.S.C. 154(b) by 0 days.

(21) Appl. No.: 09/212,219

(22) Filed: Dec. 16, 1998

(30) Foreign Application Priority Data

Dec. 19, 1997 (DE) .............................................. 197 56 783

(51) Int. Cl.$^7$ ....................................................... A61B 6/04
(52) U.S. Cl. ................................................ 378/209; 5/601
(58) Field of Search ............................. 378/20, 177, 195, 378/208, 209, 179; 5/601, 607

(56) References Cited

U.S. PATENT DOCUMENTS

| | | | | |
|---|---|---|---|---|
| 4,912,754 | * | 3/1990 | Van Steenburg | 378/209 |
| 5,014,292 | * | 5/1991 | Siczek et al. | 378/195 |
| 5,048,071 | * | 9/1991 | Van Steenburg | 378/209 |
| 5,528,782 | * | 6/1996 | Pfeuffer et al. | 5/611 |

* cited by examiner

*Primary Examiner*—Robert H. Kim
*Assistant Examiner*—Drew A. Dunn
(74) *Attorney, Agent, or Firm*—Pearne & Gordon LLP

(57) ABSTRACT

A device for moving an X-ray table 1 or the like, wherein a crosshead 3 engages with a first actuator 5a of a first linear motive unit 4a, 6a, 7a, 8a, and with a second actuator 5b, which can move parallel thereto, of a second linear motive unit 4b, 6b, 7b, 8b, and that it is possible to rotate the crosshead 3 through a different speed of movement and/or direction of movement of the first actuator 5a and second actuator 5b.

12 Claims, 3 Drawing Sheets

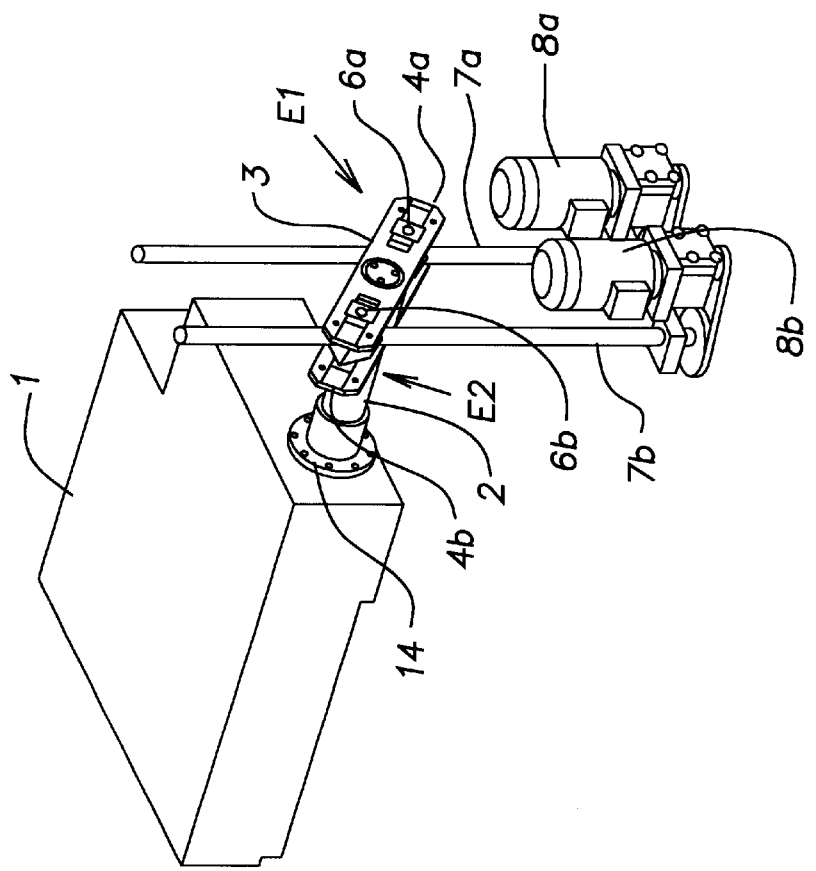
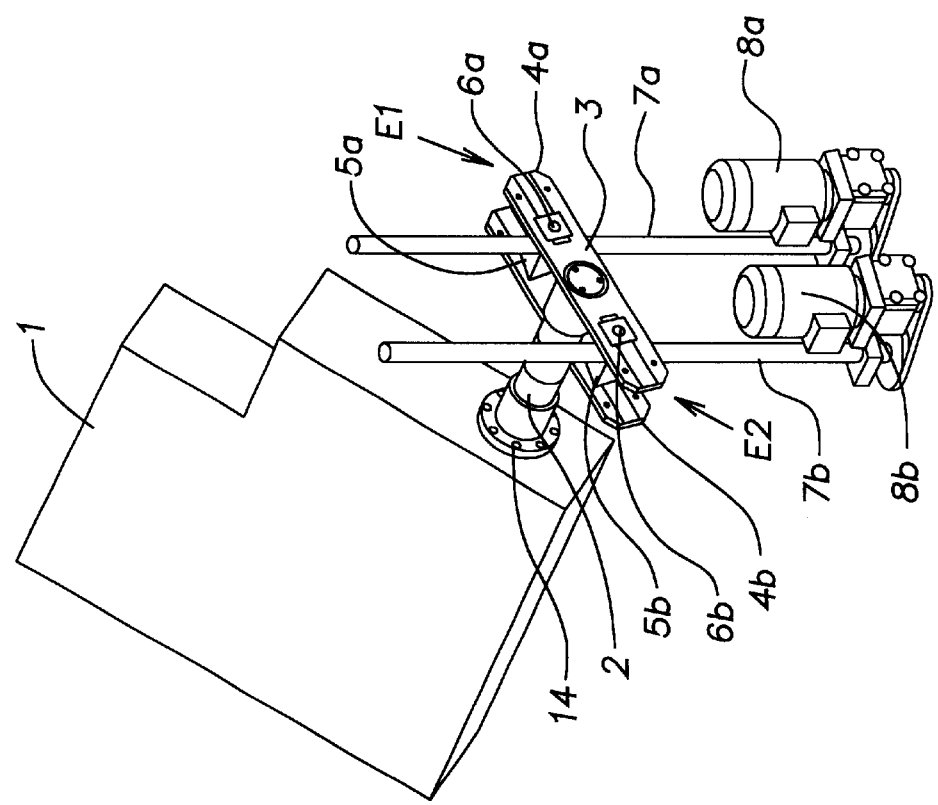

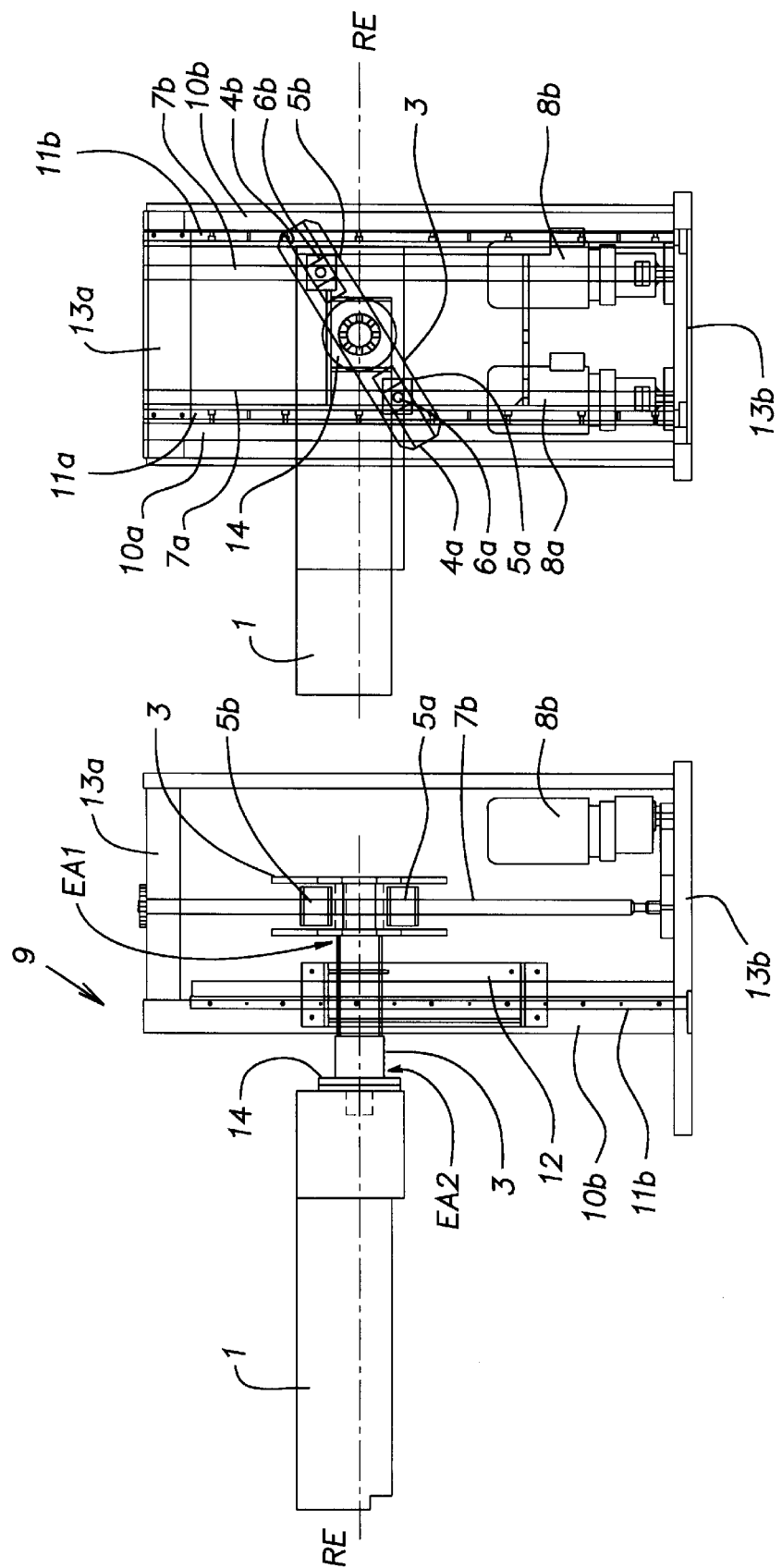

DEVICE FOR MOVING AN X-RAY TABLE OR THE LIKE

FIELD OF THE INVENTION

The invention relates to a device for moving an X-ray table or the like.

BACKGROUND OF THE INVENTION

The "UROMAT 2000" X-ray machine is known from the "UROMAT 2000" brochure from the company of Hans Pausch Röntgengerätebau GmbH+Co., 91056 Erlangen, which appeared in October 1996. In the known X-ray machine, a device is provided which can be moved vertically via a motor by means of a gear unit. The device has a further motor for pivoting an X-ray table held thereon. The known device is expensive to produce. It requires, for example, the provision of a gear unit.

BRIEF SUMMARY OF THE INVENTION

It is the object of the invention to specify a device, which can be produced as simply and cost-effectively as possible, for moving an X-ray table or the like.

This object is achieved by means of the features of claim 1. Expedient developments of the invention follow from the features of claims 2 to 13.

According to the invention, a device is provided for moving an X-ray table or the like, it being the case that a rotation means engages with a first actuator of a first linear motive unit, and with a second actuator, which can move parallel thereto, of a second linear motive unit, and that it is possible to rotate the rotation means through a different speed of movement and/or direction of movement of the first actuator and second actuator. The device is of simple construction. There is no longer any need for a gear.

According to one embodiment feature, the axis of rotation of the rotation means is essentially perpendicular to the direction of movement of the actuators. The rotation means can be moved linearly in the same speed of movement and direction of movement of the actuators. If the actuators can be moved vertically, the rotation means can be moved up and down vertically in a simple way.

In an expedient way, the first linear motive unit has a first sliding block engaging in the thread of a first driven screw, and the second linear motive unit has a second sliding block engaging in the thread of a second driven screw. The rotation means can have an axle on whose one end a crosshead is provided. In an expedient way, the first sliding block is displaceably held in a first slideway provided at a first end of the crosshead, and the second sliding block is displaceably held in a second slideway provided at the second end of the crosshead. This permits a rotary movement of the crosshead in conjunction with a different speed of movement and/or direction of movement of the first and second actuators. This embodiment has the advantage of being self inhibiting, that is to say any further movement is stopped in the event of a power failure.

It is possible to provide at the other end of the axle a means, in particular a flange, for fastening an X-ray table, X-ray table support or the like. In order in the case of a horizontal arrangement of the axle to absorb the tilting moment caused by the weight of an X-ray table or X-ray table support fastened thereto, the axle is advantageously mounted in a linearly displaceable carriage. The carriage is expediently held on two parallel vertical frame uprights.

In order to permit movement of the X-ray table into a prescribed position, it is expediently the case that the first sliding block and/or the second sliding block is/are provided with a displacement sensor, with the result that the position and/or the angle of rotation of the axle can be determined. Furthermore, it is the case that a control element which can be actuated by the first or second sliding block can be provided at least at one of the ends, averted from the axle, of the slideways. As a result, the rotary movement of the axle can be stopped automatically.

According to a further embodiment feature, it is the case that, with the X-ray table perpendicular to the screws, the crosshead forms an angle of 25 to 40°, preferably of 35°, with respect to an X-ray table plane. As a result, the rotary movement of the X-ray table can be adapted to the practical requirements. The X-ray table can, in an expedient way, be held in a movable fashion in the X-ray table plane on an X-ray table support.

The following discussion relates to an embodiment feature which is to be regarded as a further invention both in combination with the abovementioned invention and per se. An X-ray image intensifier can be included in the X-ray table support. The X-ray image intensifier is provided in the vicinity of one transverse side of the X-ray table support. This permits a particularly simple transillumination of the patient when the latter is seated in the vicinity of one transverse side of the X-ray table support. The particularly advantageous arrangement of the X-ray image intensifier is permitted by virtue of the fact that a film cassette holder can be moved in the X-ray table support parallel to the longitudinal side thereof. An opening for loading and unloading of the film cassette holder is located in the vicinity of the other transverse side on the front longitudinal side of the X-ray table support.

BRIEF DESCRIPTION OF THE SEVERAL VIEWS OF THE DRAWINGS

An exemplary embodiment of the invention is explained in more detail below with the aid of the drawing, in which:

FIG. 1 shows a first perspective view of the device,

FIG. 2 shows a second perspective view of the device,

FIG. 3 shows a first side view of the device with a frame,

FIG. 4 shows a second side view according to FIG. 3, and

DETAILED DESCRIPTION OF THE INVENTION

Figure 5:
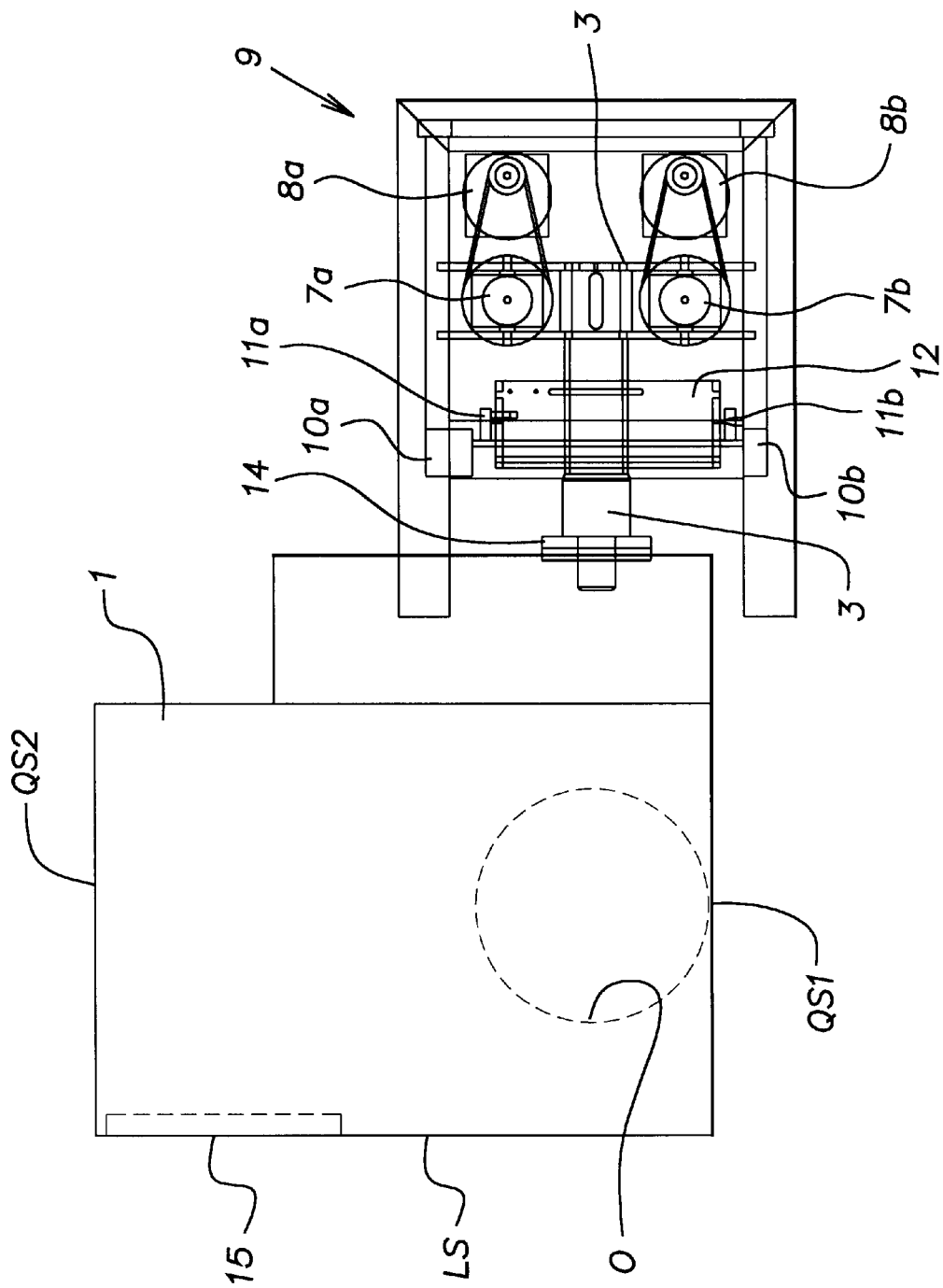
FIG. 5 shows a plan view according to FIG. 3.

FIGS. 1 and 2 show perspective views of the device without a frame. An X-ray table support 1 is connected to a crosshead 3 via an axle 2. The crosshead 3 here comprises two parallel plates, at whose first ends E1 and second ends E2 first slideways 4a and second slideways 4b are respectively provided. First sliding elements 6a and second sliding elements 6b are guided displaceably in the slideways 4a, 4b. The first sliding elements 6a are fitted rotatably on a first sliding block 5a, and the second sliding elements 6b are fitted on a second sliding block 5b.

The first sliding block 5a engages with the thread of a first screw 7a; the second sliding block 5b engages with the thread of a second screw 7b. A first electric motor 8a is connected by means of a toothed belt to the first screw 7a, while a second electric motor is connected by means of a further toothed belt to the second screw 7b.

FIGS. 3 to 5 show side views and a plan view of the device according to FIGS. 1 and 2, said device being held in a frame 9. Guide rails 11a, 11b in which a carriage 12 is guided in a movable fashion are fastened to two front uprights 10a, 10b of the frame 9. The axle 2 is mounted in the carriage 12. The first screw 7a and the second screw 7b are mounted rotatably in an upper transom 13a and a lower transom 13b of the frame 9. The axle 2 is welded to the crosshead 3 at one end EA1. Provided at the other end EA2 of the axle 2 is a flange 14 on which the X-ray table support 1 is mounted.

As may be seen from FIG. 5, the X-ray table holder 1 has a first transverse side QS1 and a second transverse side QS2, as well as a front longitudinal side LS. An opening O for holding an X-ray image intensifier is provided in the X-ray table support 1. A loading and unloading opening 15 for film cassettes is arranged in the vicinity of the second transverse side QS2 of the front longitudinal side LS. An X-ray source (not shown here) is provided above the X-ray table support 1.

The device functions as follows:

Given rotation of the screws 7a and 7b in the same sense and at the same speed, the sliding blocks 5a, 5b, which are held in a rotationally fixed fashion in the crosshead 3, are moved upward and downward vertically at the same speed.

When one of the two screws 7a or 7b is moved in the opposite sense of rotation and/or a different rotational speed than the other screw 7b or 7a, the sliding block 5a or 5b, respectively, engaging therewith is displaced relative to the other sliding block 5b or 5a. The crosshead 3 is rotated thereby. The changes effected in this case in the spacing between the two sliding blocks 5a and 5b is compensated by the sliding movement of the sliding elements 6a and 6b in the slideways 4a and 4b.

In the exemplary embodiment shown, given an X-ray table plane RE which is perpendicular to the screws 7a, 7b, the crosshead 3 forms an angle of approximately 35°. It is therefore possible to pivot the X-ray table support 1 in one direction by approximately 20° and in the other direction by approximately 80° to adapt to the practical requirements. An X-ray table (not shown here) is held on the X-ray table support 1. The X-ray table can be displaced in the X-ray table plane RE.

List of reference symbols
1 X-ray table support
2 Axle
3 Crosshead
4a, 4b First, second slideway
5a, 5b First, second sliding block
6a, 6b Fist, second sliding element
7a, 7b First, second screw
8a, 8b First, second electric motor
9 Frame
10a, 10b Front uprights
11a, 11b Guide rails
Carriage
13a Upper transom
13b Lower transom
14 Flange
15 Loading and unloading opening
E1 First end
E2 Second end
RE X-ray table plane
EA1 First end of the axle
EA2 Second end of the axle
QS1 First transverse side
QS2 Second transverse side
LS Front longitudinal side

What is claimed is:

1. Device for moving an X-ray table comprising a rotation means (3) being in engagement with a first sliding block (5a) of a first linear motive unit (4a, 6a, 7a, 8a), and with a second sliding block (5b) of a second linear motive unit (4b, 6b, 7b, 8b);

wherein the first sliding block is capable of movement along the first linear motive unit and the second sliding block is capable of movement along the second linear motive unit;

wherein the first linear motive unit has the first sliding block (5a) engaging the thread of a first driven screw (7a), and the second linear motive unit has the second sliding block (5b) engaging the thread of a second driven screw (7b) that is parallel to the first driven screw; and wherein the rotation means (3) is caused to rotate solely by parallel movement of the first sliding block (5a) and second sliding block (5b) relative to one another.

2. Device according to claim 1, wherein the axis of rotation of the rotation means (3) is essentially perpendicular to the direction of movement of the sliding blocks (5a, 5b).

3. Device according to claim 1 or 2, wherein the rotation means (3) can be moved linearly in the same speed of movement and direction of movement of the sliding blocks (5a, 5b).

4. Device according to claim 1, wherein the rotation means (3) has an axle (2) on whose one end (EA1) a crosshead (3) is provided.

5. Device according to claim 4, wherein the first sliding block (5a) is displaceably held in a first slideway (4a) provided at a first end (E1) of the crosshead (3), and the second sliding block (5b) is displaceably held in a second slideway (4b) provided at a second end (E2) of the crosshead (3).

6. Device according to claim 4 or 5, wherein a means, in particular a flange (4), for fastening an X-ray table, X-ray table support (1), is provided at a second end (E2) of the axle (2).

7. Device according to claim 4, wherein the axle (2) is mounted in a linearly displaceable carriage (12).

8. Device according to claim 4, wherein the first sliding block (5a) and/or the second sliding block (5b) is/are provided with a displacement sensor, with the result that the position and/or the angle of rotation of the axle (2) can be determined.

9. Device according to claim 4, wherein a control element which can be actuated by the displacement movement of the first or second sliding block (5a, 5b) is provided at least at one of the end, averted from the axle (2), of the slideways (4a, 4b).

10. Device according to claim 1, wherein, with the X-ray table (1) perpendicular to the screws (7a, 7b), the crosshead (3) forms an angle of 25 to 40°, preferably of 35°, with respect to an X-ray table plane (RE).

11. Device according to claim 1, wherein an X-ray table held on the X-ray table support (1) can be moved in an X-ray table plane (RE).

12. Device according to claim 1, wherein there is provided in the X-ray table support (1) a film cassette holder which can be moved parallel to the longitudinal side thereof.

* * * * *